(12) United States Patent
Tan et al.

(10) Patent No.: US 7,611,895 B2
(45) Date of Patent: *Nov. 3, 2009

(54) METHOD FOR GROWTH OF HUMAN CONJUNCTIVAL TISSUE EQUIVALENTS FOR RESEARCH, CLINICAL OCULAR SURFACE TRANSPLANTATION AND TISSUE ENGINEERING

(75) Inventors: Donald Tan, Singapore (SG); Leonard Ang, Singapore (SG); Roger Beuerman, New Orleans, LA (US)

(73) Assignee: Singapore Eye Research Institute, Singapore (SG)

( * ) Notice: Subject to any disclaimer, the term of this patent is extended or adjusted under 35 U.S.C. 154(b) by 308 days.

This patent is subject to a terminal disclaimer.

(21) Appl. No.: 11/398,557

(22) Filed: Apr. 6, 2006

(65) Prior Publication Data

US 2006/0177927 A1   Aug. 10, 2006

Related U.S. Application Data

(62) Division of application No. 10/401,788, filed on Mar. 31, 2003, now Pat. No. 7,049,139.

(60) Provisional application No. 60/368,158, filed on Mar. 29, 2002.

(51) Int. Cl.
*C12N 5/06* (2006.01)
*C12N 5/08* (2006.01)

(52) U.S. Cl. .................. 435/371; 435/366; 435/375; 435/377; 435/404

(58) Field of Classification Search .................. None
See application file for complete search history.

(56) References Cited

U.S. PATENT DOCUMENTS

| | | | |
|---|---|---|---|
| 3,249,504 A | 5/1966 | Cappel et al. | |
| 4,423,145 A | 12/1983 | Stampfer et al. | |
| 4,443,546 A | 4/1984 | Stemerman et al. | |
| 4,456,687 A | 6/1984 | Green | |
| 4,673,649 A | 6/1987 | Boyce et al. | |
| 4,940,666 A | 7/1990 | Boyce et al. | |
| 5,063,157 A | 11/1991 | Stockinger | |
| 5,166,048 A | 11/1992 | Soll et al. | |
| 5,292,655 A | 3/1994 | Wille, Jr. | |
| 5,326,699 A | 7/1994 | Torishima et al. | |
| 5,328,844 A | 7/1994 | Moore | |
| 5,342,777 A | 8/1994 | Cole et al. | |
| 5,405,772 A | 4/1995 | Ponting | |
| 5,610,281 A | 3/1997 | Brenner et al. | |
| 5,610,699 A | 3/1997 | Yu et al. | |
| 5,612,028 A | 3/1997 | Sackier et al. | |
| 5,686,307 A | 11/1997 | Wille, Jr. | |
| 5,712,163 A | 1/1998 | Parenteau et al. | |
| 5,795,781 A | 8/1998 | Wille, Jr. | |
| 5,811,094 A | 9/1998 | Caplan et al. | |
| 5,834,312 A | 11/1998 | Wille, Jr. | |
| 5,912,175 A | 6/1999 | Wille, Jr. | |
| 5,932,205 A | 8/1999 | Wang et al. | |
| 6,043,092 A | 3/2000 | Block | |
| 6,045,791 A | 4/2000 | Liu | |
| 6,117,675 A | 9/2000 | van der Kooy et al. | |
| 6,143,315 A | 11/2000 | Wang et al. | |
| 6,326,019 B1 | 12/2001 | Tseng | |
| 7,049,139 B2 * | 5/2006 | Tan et al. ............... | 435/371 |
| 2002/0039788 A1 * | 4/2002 | Isseroff et al. ........... | 435/366 |

OTHER PUBLICATIONS

Koizumi et al., Abstract of "Amniotic Membrane as a Substrate for Cultivating Limbal Corneal Epithelail Cells for Autologous Transplantation in Rabbits", Cornea, vol. 19, No. 1, Jan. 2000, pp. 65-71.
Geggel et al., Abstract of "Removal of Viable Sheets of Conjunctival Epithelium with Dispase II", Invest Ophtamol Vis Scie, vol. 26, No. 1, Jan. 1985, pp. 15-22.
Meller et al., "Conjunctival epithelial cell differentiation on Amniotic Membrane", Investigative Ophthalmology & Visual Science, Apr. 1999, vol. 40, No. 5 pp. 878-886.
Pellegrini et al., "Long term restoration of damaged corneal surfaces with autologous cultivated corneal epithelium", Lancet, Apr. 1997, vol. 349, pp. 990-993.
Wei et al., "In Vitro Growth and Differentiation of Rabbit Bulbar, Fornix, and Palpebral Conjunctival Epithelia", Investigative Ophthalmology and Visual Science, Apr. 1993, vol. 34, No. 5, pp. 1814-1827.

* cited by examiner

*Primary Examiner*—Vera Afremova
(74) *Attorney, Agent, or Firm*—Birch, Stewart, Kolasch & Birch, LLP.

(57) ABSTRACT

The invention relates to materials and methods for producing equivalents of tissues of the ocular surface, especially conjunctival tissue equivalents. The method of the invention involves biopsy of an appropriate tissue, primary culture in a certain medium, proliferative culture in a second medium, and differentiative culture in a third medium. The tissue equivalents are typically grown upon a substrate, typically amniotic membrane, which provides ease of handling as one advantage.

6 Claims, 13 Drawing Sheets

METHOD FOR GROWTH OF HUMAN CONJUNCTIVAL TISSUE EQUIVALENTS FOR RESEARCH, CLINICAL OCULAR SURFACE TRANSPLANTATION AND TISSUE ENGINEERING

This application is a Divisional of application Ser. No. 10/401,788, filed on Mar. 31, 2003, now U.S. Pat. No. 7,049,139 the entire contents of which are hereby incorporated by reference and for which priority is claimed under 35 U.S.C. § 120. The Nonprovisional application Ser. No. 10/401,788 claims priority under 35 U.S.C. § 119(e) on U.S. Provisional Application No(s). 60/368,158 filed on Mar. 29, 2002, the entire contents of which are hereby incorporated by reference.

FIELD OF THE INVENTION

The present invention relates to a method for culturing conjunctival stem cells in vitro to form conjunctival epithelial tissue equivalents by expanding the explanted conjunctival stem cells and then differentiating them in culture. The present invention also relates to culture media for supporting such a method. The present invention also encompasses methods for treating eye disorders by transplanting tissue equivalents comprising conjunctival epithelial cells.

BACKGROUND OF THE INVENTION

R. J.-F. Tsai et al. (*NEJM* 343:86 (2000), I. R. Schwab et al. (*Cornea* 19:421 (2000) and G. Pellegrini et al. (*The Lancet* 349:990 (1997)) describe transplanting limbal stem cells for diseases arising from limbal stem cell deficiency to restore corneal epithelial integrity.

The Tsai paper mentions that conjunctival epithelial cells are an integral part of the eye surface, but Tsai et al. and other papers on limbal stem cell transplantation indicate that (i) the conjunctival and corneal cell types are quite different in function and morphology, with the limbal cells being the progenitor of corneal cells; and (ii) to achieve regeneration of the corneal surface, the important stem cell type to transplant is the limbal stem cell. Tsai et al. and others fail to suggest that conjunctival epithelium is useful in restoring the corneal surface. The limbal stem cell is indeed an important factor in restoring the corneal surface, but conjunctival stem cells are important in preventing limbal stem cell and corneal epithelial damage in the first place. This is due to the supportive function of conjunctival stem cells, which is important to regeneration and restoration of the ocular surface.

Z-G. Wei et al. (*Investigative Ophthalmology and Visual Science* 34:1814 (1993)) describe the origin of conjunctival stem cells at the fornix. Y. Diebold et al. (*Graefe's Arch. Clin. Exp. Ophthalmol.* 233:268 (1997)) describe primary culture of cells from forniceal conjunctiva tissue.

DETAILED DESCRIPTION OF THE INVENTION

Figure 1:
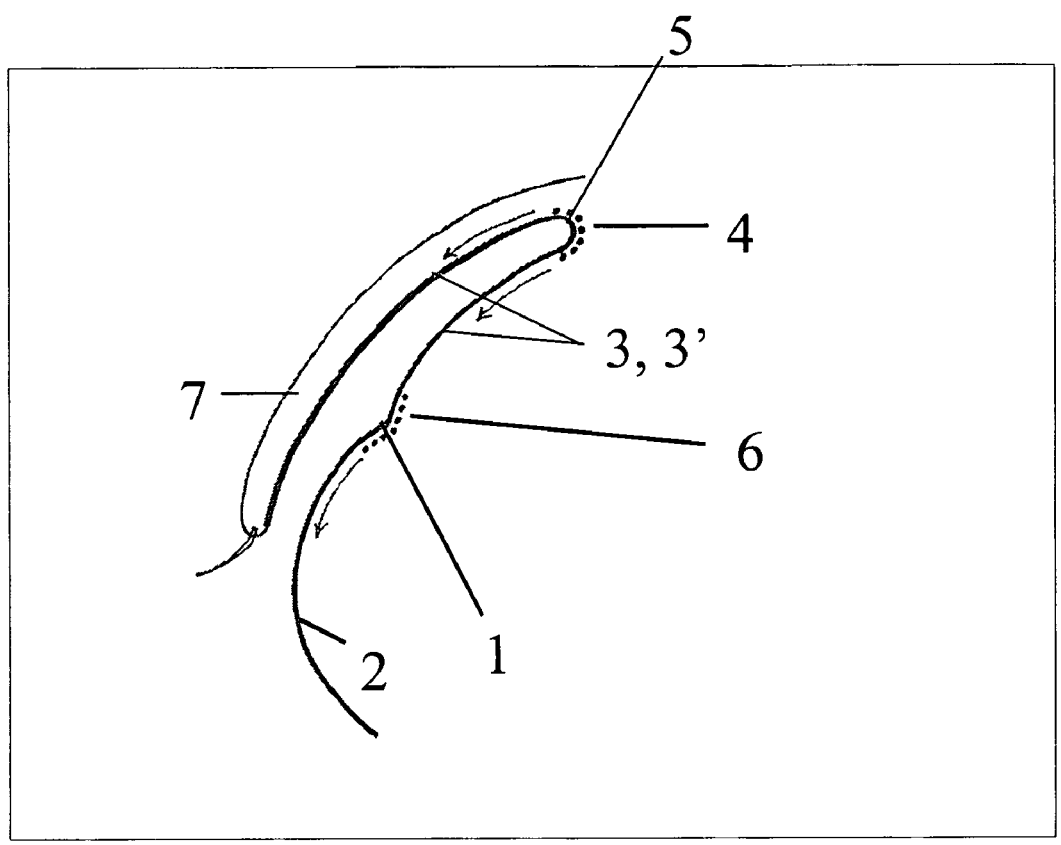
FIG. 1 shows a schematic cross section of the eyeball, illustrating the location of the limbal region (1) at the junction of the cornea (2) and the conjunctiva (3, 3') at the periphery of the eyeball and on the inner surface of the eyelid (7). Conjunctival stem cells (4) are located at the fornix (5) at the top of the eyeball. Limbal stem cells (6) are located in the limbal region.
Figure 2A:
FIG. 2A shows a phase contrast micrograph of a primary explant of a conjunctival tissue biopsy, showing confluent outgrowth of cells from the explant.
Figure 2B:
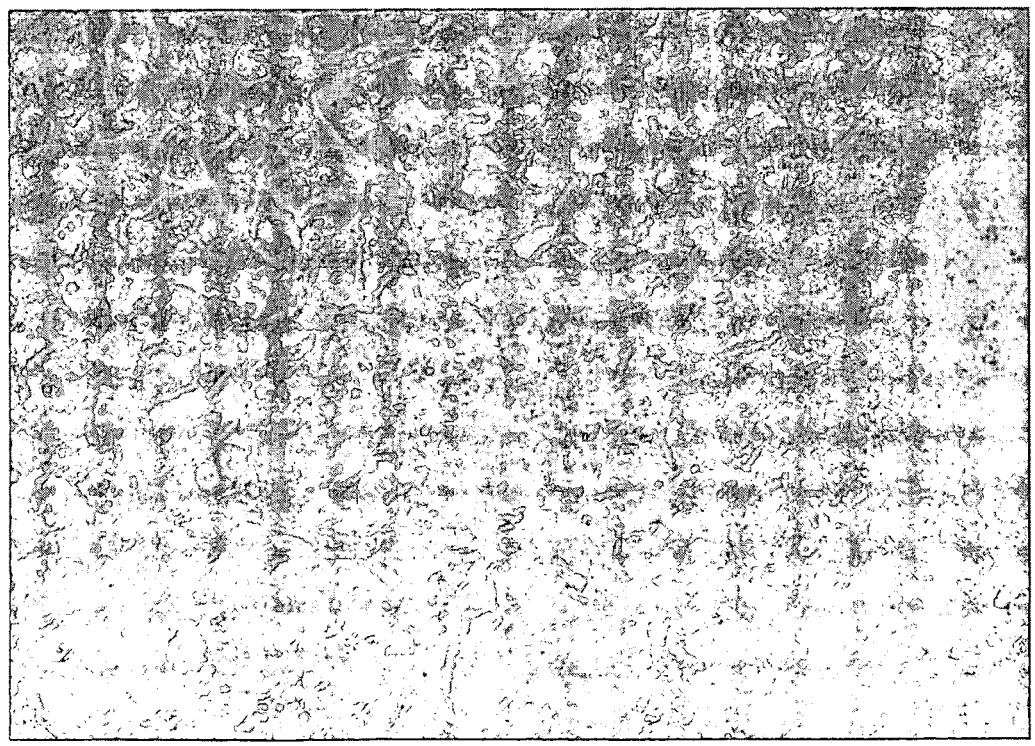
FIG. 2B is a higher magnification of a portion of the culture shown in FIG. 2A.
Figure 2C:
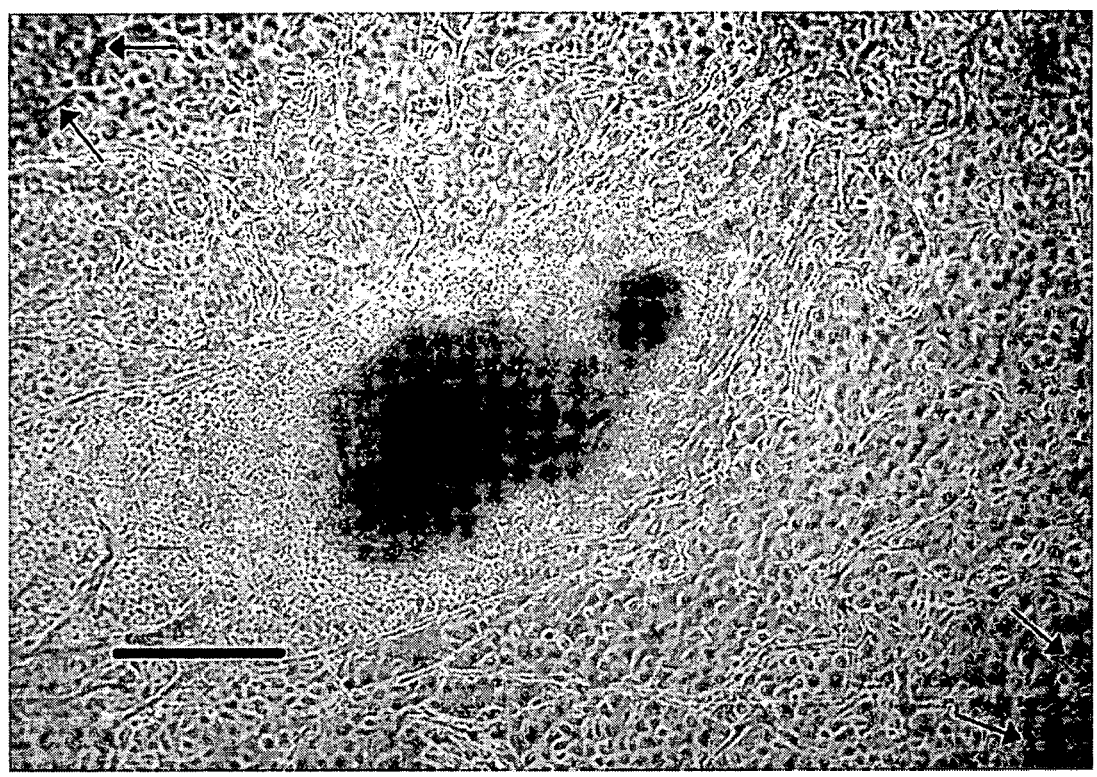
FIG. 2C is a phase contrast micrograph of a primary conjunctival explant culture on a human amniotic membrane substrate. The arrows indicate the edge of the epithelial sheet that has migrated from the explant.
Figure 3A:
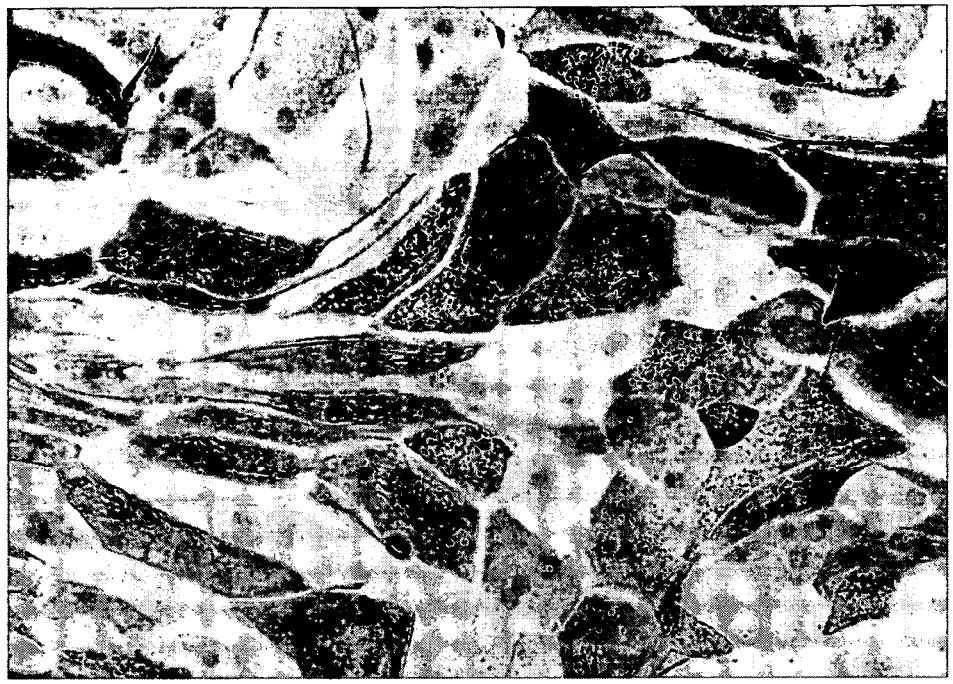
FIG. 3A shows differentiated conjunctival epithelial cells of the invention stained for cytokeratin K4. Staining was performed by methods typical in the art, as described by K. L. Krenzer and T. F. Freddo (*Investigative Ophthalmology and Visual Science* 38:142 (1997)) using mouse monoclonal antibody to cytokeratin K4. The cell bodies are positively stained.
Figure 3B:
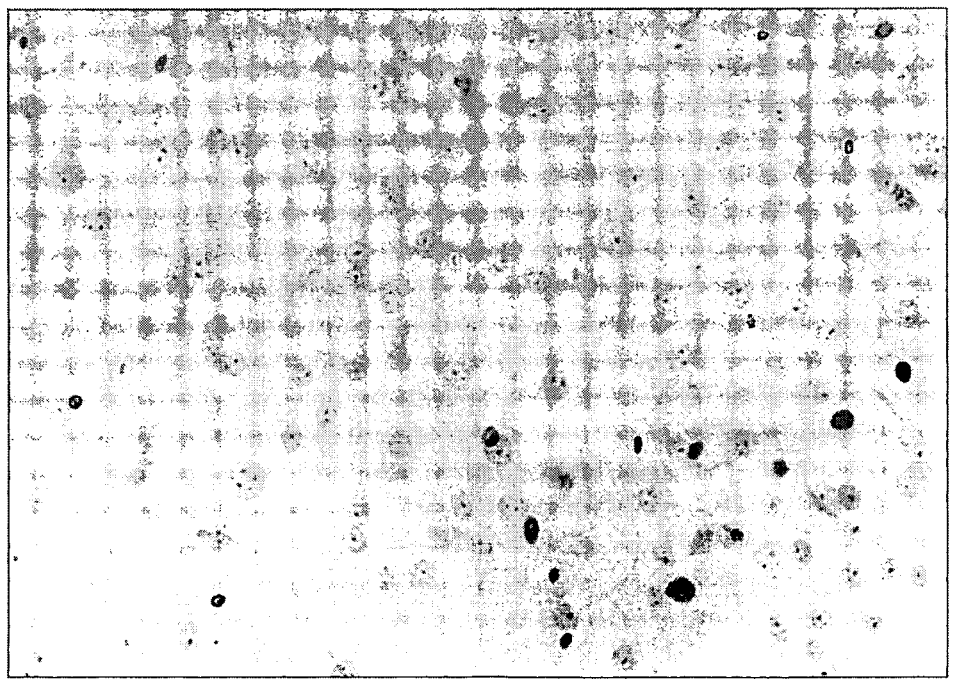
FIG. 3B shows differentiated conjunctival epithelial cells of the invention stained for cytokeratin K3. Staining was performed as described above, but using the AE-5 monoclonal antibody to cytokeratin K3 from mouse. The conjunctival epithelial cells do not express the corneal specific keratin, K3. The cell bodies are not stained.
Figure 4A:
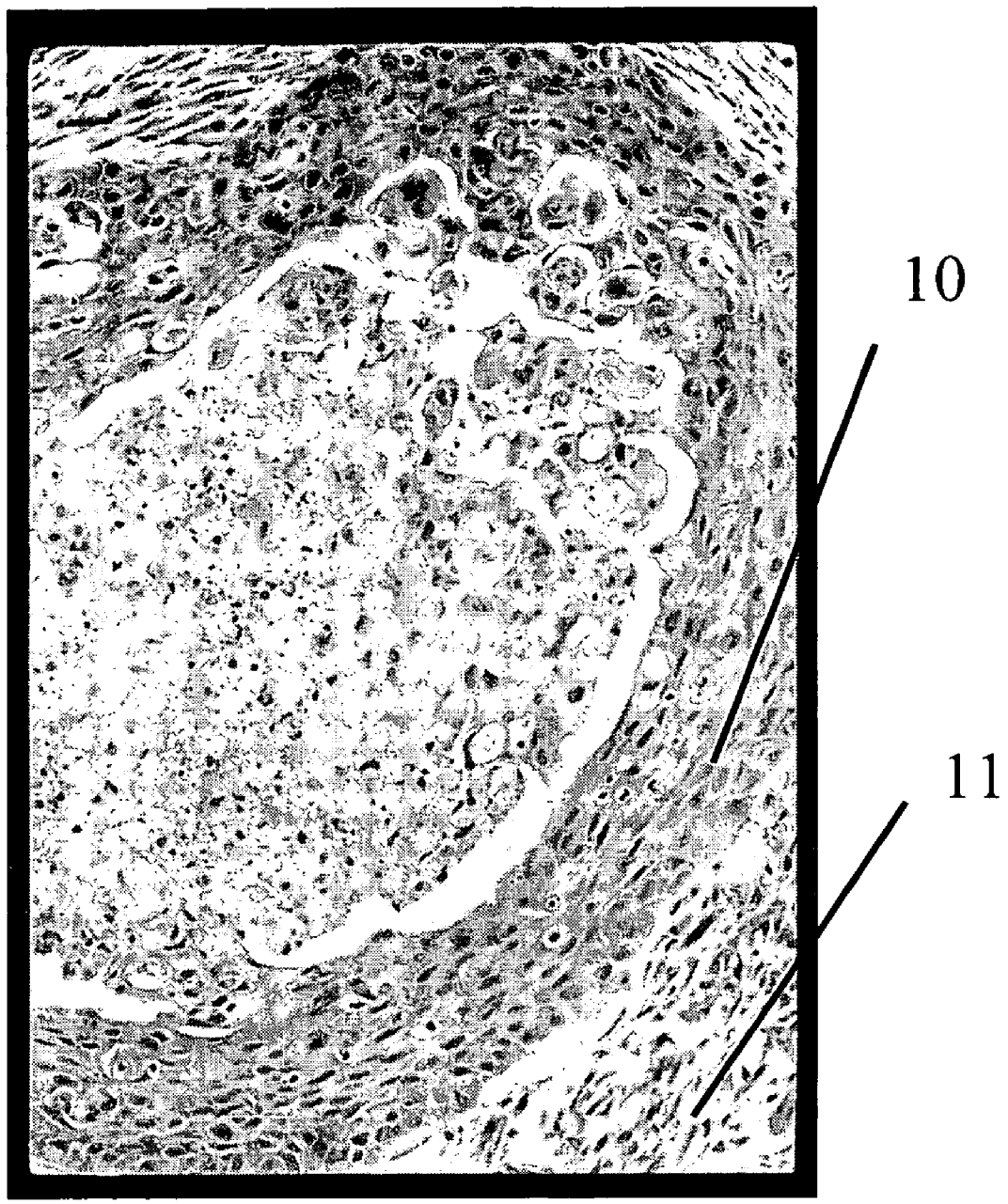
FIG. 4A is a low magnification light micrograph of a cyst derived from cultured conjunctival epithelial cells injected subcutaneously into the flanks of athymic mice. The stratified squamous epithelium arising from the transplant (10) is bounded by the edge of the cyst consisting of mouse stroma (11).
Figure 4B:
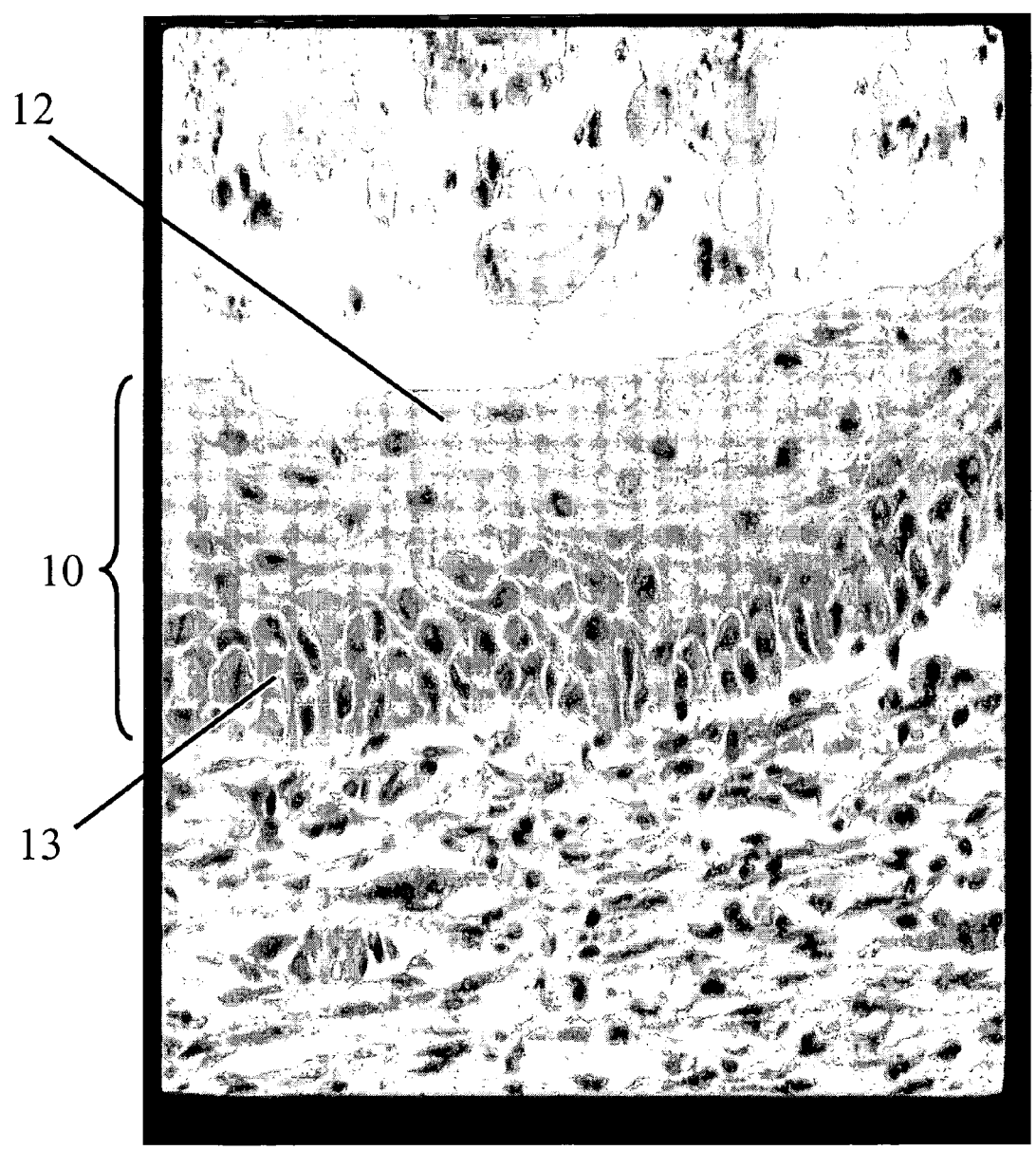
FIG. 4B is a higher magnification of a portion of the cyst shown in FIG. 4A. The appearance of a stratified squamous epithelium (10) consisting of a superficial cell layer (12) and basal cells (13) is clear.
Figure 5A:
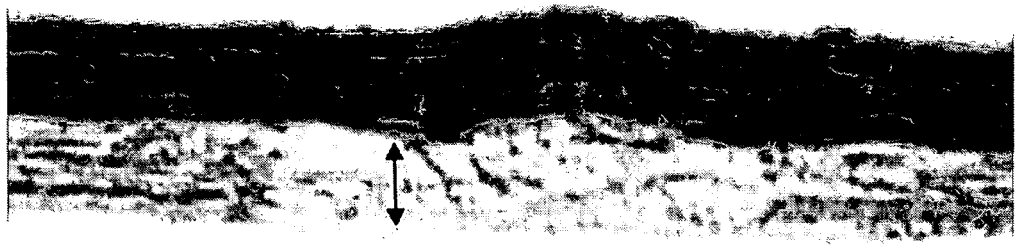
FIG. 5A is light micrograph of a cross section of a conjunctival tissue equivalent showing the epithelial cells growing upon a human amniotic membrane substrate. Human amniotic membrane is the lower section within the area indicated by the double headed arrow.
Figure 5B:
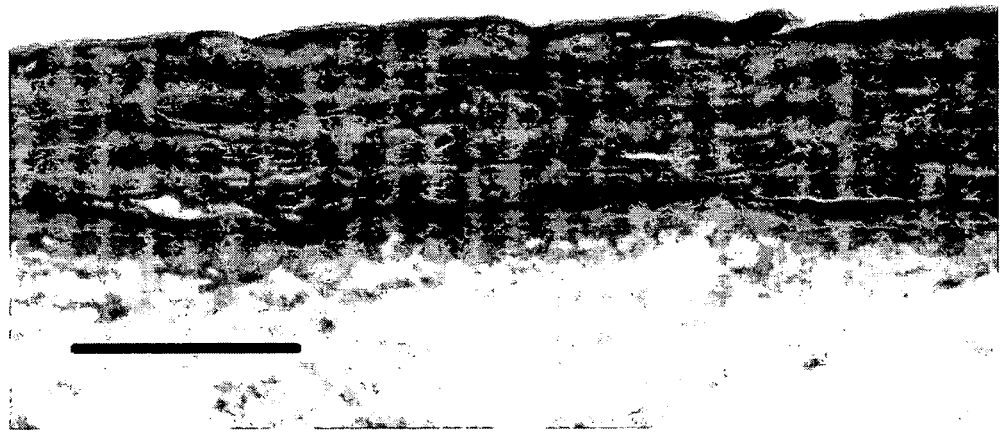
FIG. 5B is an immunostaining of conjunctival tissue-equivalent demonstrating positive staining with cytokeratin K4 antibody.
Figure 5C:
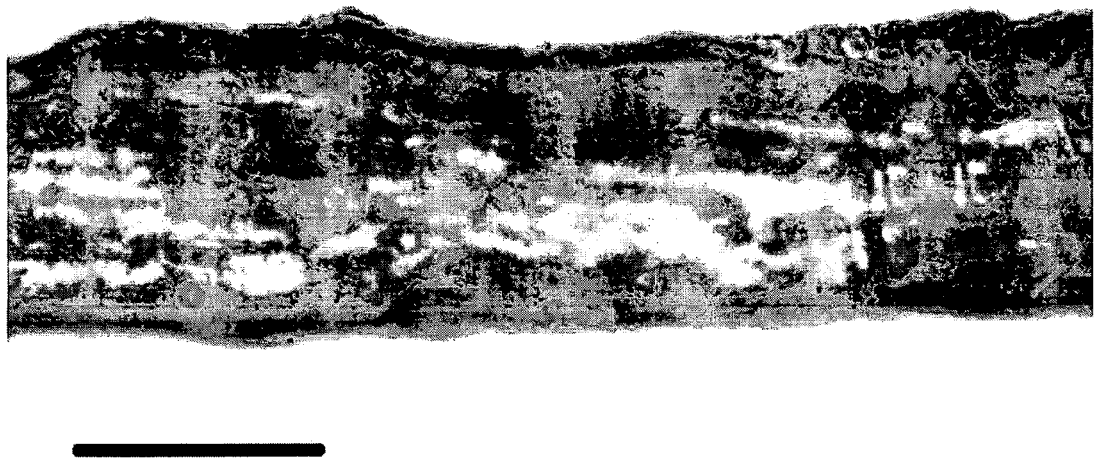
FIG. 5C is an immunostaining of conjunctival tissue-equivalent demonstrating non-staining with cytokeratin K3 antibody. Scale bar=63 mm.
Figure 6A:
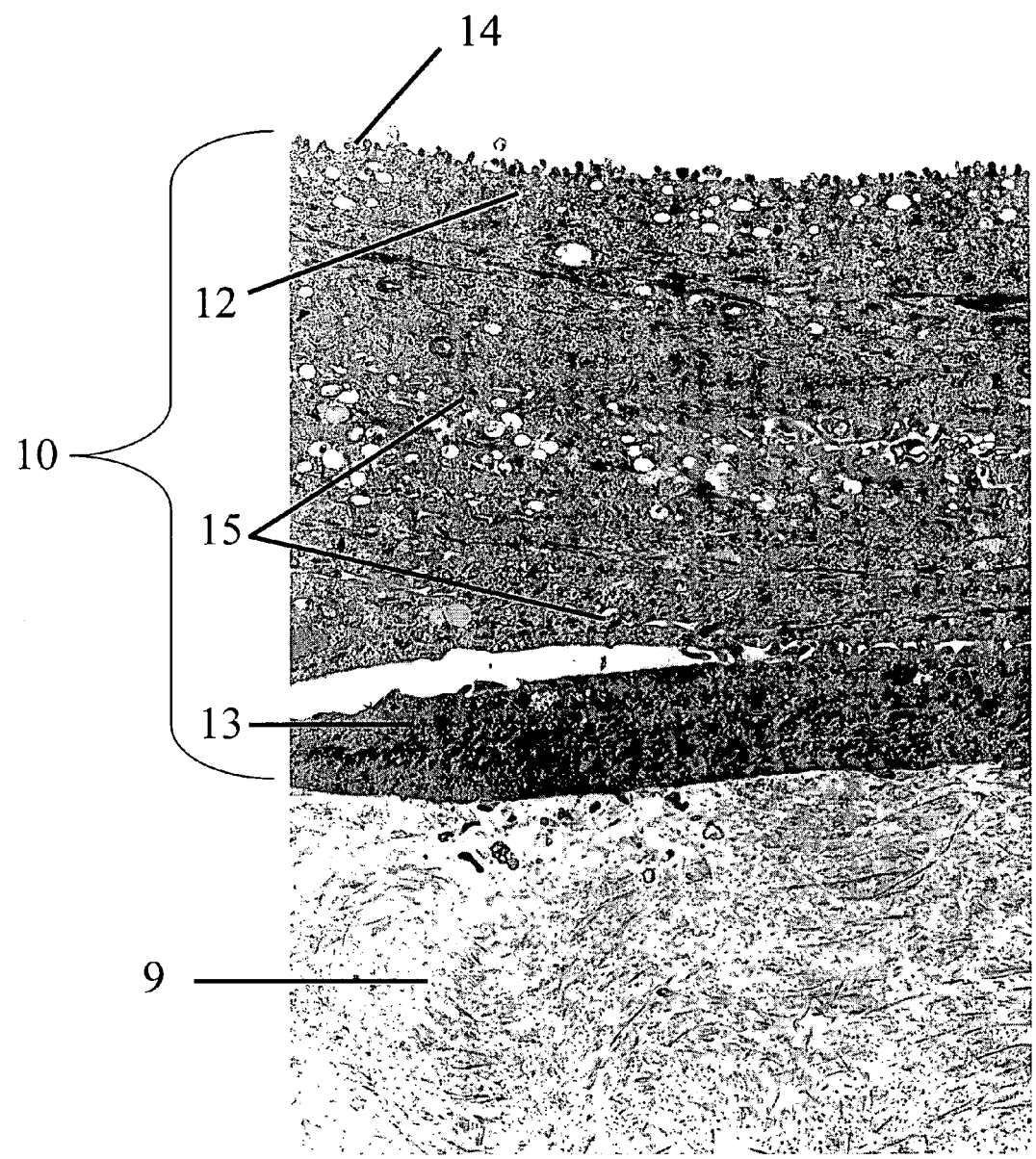
FIG. 6A shows an electron micrograph of multi-layered cultured conjunctival epithelium on a human amniotic membrane substrate. The multilayered conjunctival epithelium comprising a layer of superficial cells (12) expressing a surface layer of microvillus extensions (14) and basal cells (13) is shown lying on a human amniotic membrane substrate (9). Numerous desmosomes (adhesion structures) are present (15).
Figure 6B:
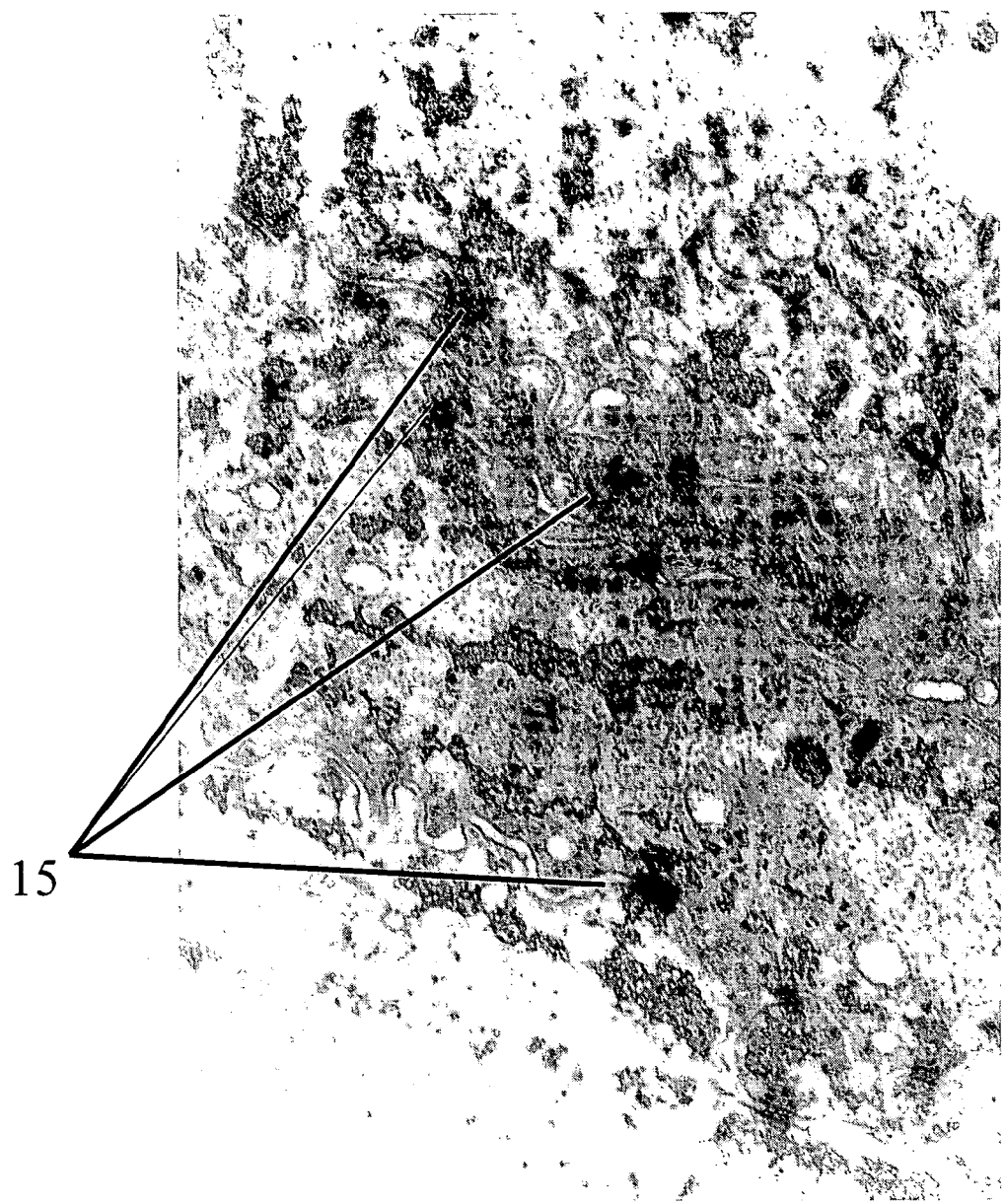
FIG. 6B is a higher magnification electron micrograph of multi-layered cultured conjunctival epithelium on a human amniotic membrane substrate. This figure shows the presence of desmosome adhesion structures (15).
Figure 7:
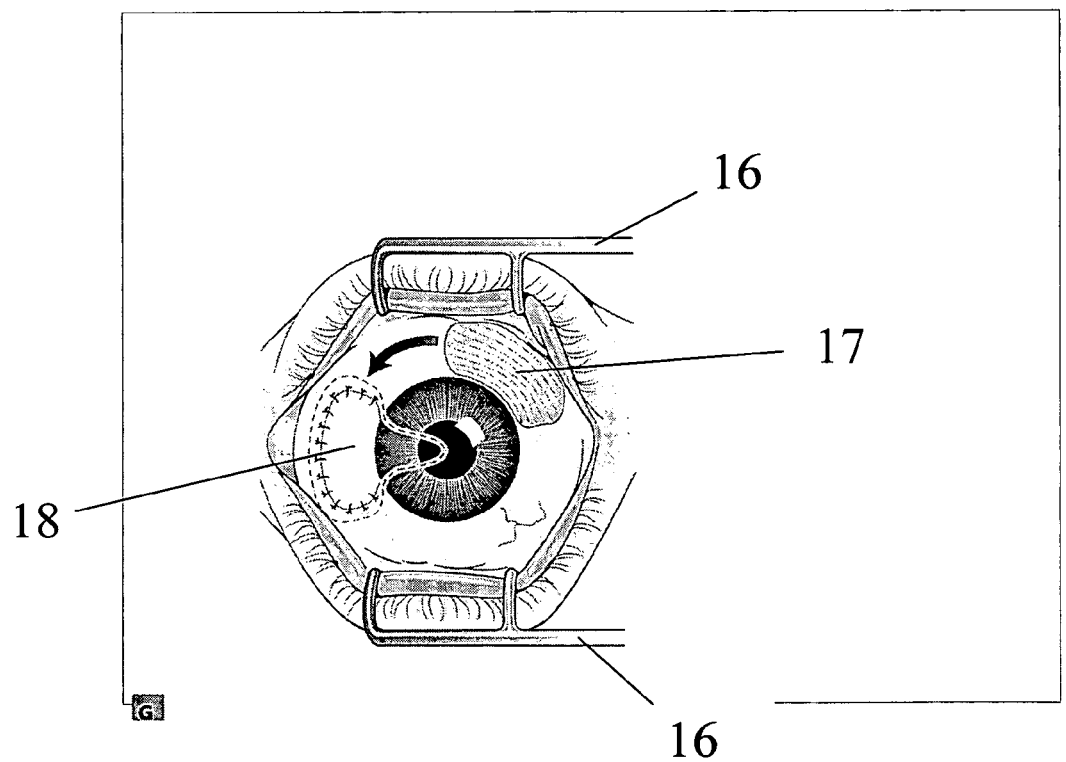
FIG. 7 is a schematic drawing of the result of conventional pterygium excision followed by a large autograft of conjunctival tissue harvested from superior bulbar conjunctiva; the placement of the speculum (16), the superior bulbar conjunctival harvest site (17) and the conjunctival graft sutured in place at the excised pterygium site (18) is shown.
Figure 8A:
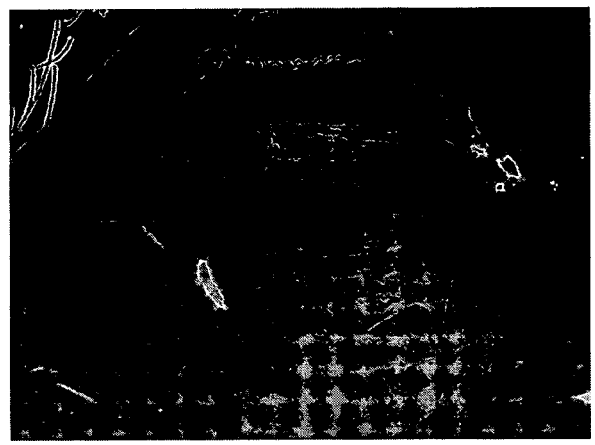
FIG. 8A is a preoperative photograph of a clinical trial patient depicting a nasally situated pterygium.
Figure 8B:
FIG. 8B is an early postoperative photograph of the clinical trial patient showing the placement of the conjunctival equivalent prepared according to the invention. The photograph also shows a patch of amniotic membrane placed over the conjunctival equivalent to protect the graft during healing.
Figure 8C:
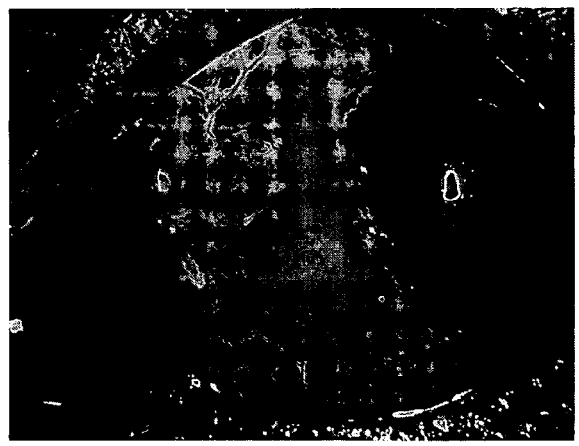
FIG. 8C is a photograph of the transplant of FIG. 8B taken one month postoperatively. The graft shows an excellent "take" with restoration of limbal and conjunctival anatomy.
Figure 9A:
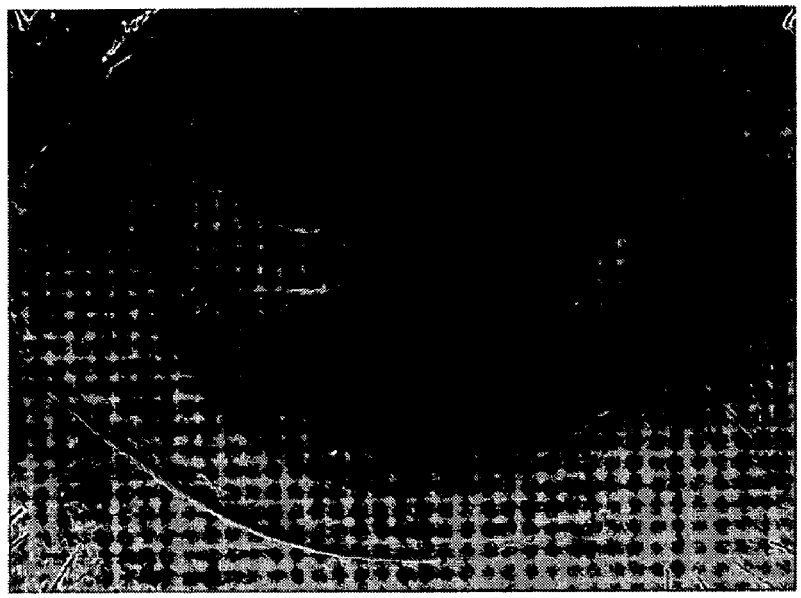
FIG. 9A is a preoperative photograph of a second clinical trial patient showing both nasally and temporally situated pterygium.
Figure 9B:
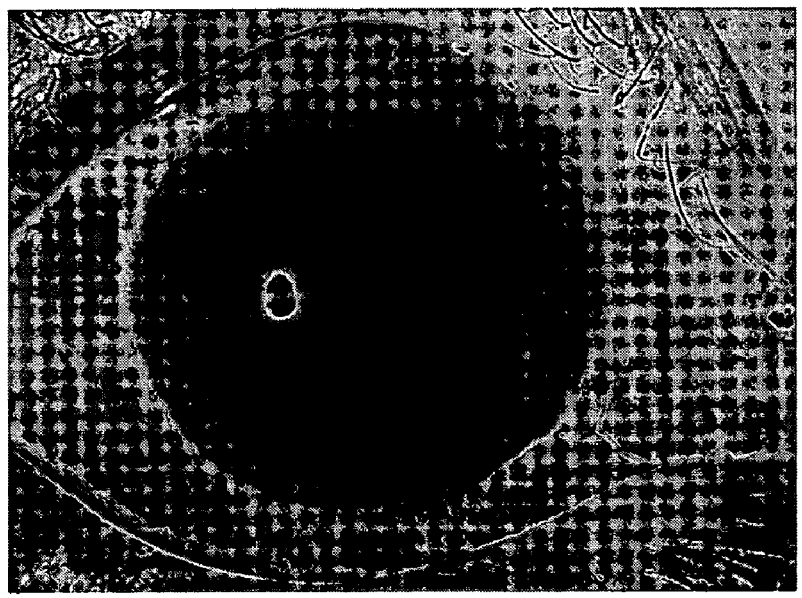
FIG. 9B is a postoperative photograph of the patient shown in FIG. 9A, taken one month after surgery. The excellent functional and cosmetic result of both conjunctival equivalent grafts, with restoration of limbal and conjunctival anatomy and no evidence of recurrence of the pterygium, is shown.

The Ocular Surface consists of two basic epithelial surfaces, corneal epithelium (which covers the cornea) and conjunctival epithelium, which covers the sclera, and inner surfaces of the eyelids (See FIG. 1). A stem cell population, which continually replaces corneal epithelium, resides at the limbus and are known as Limbal Stem Cells (LSC). On the other hand, stem cells that continually replace conjunctival epithelium have been shown, in the rabbit eye, to reside at the conjunctival fornix. These stem cells, which lie at the uppermost and (probably) lowermost regions of the conjunctiva at the forniceal junction between the sclera and the eyelids, are known as Conjunctival Stem Cells (CSC). Mucin-producing goblet cells, interspersed between conjunctival epithelial cells on the conjunctival surface, are also purported to be derived from the bipotent adult CSC. The LSC and CSC stem cell groups are located far from each other on the ocular surface.

Furthermore, corneal and conjunctival epithelial cells appear to belong to two different lineages (Z. G. Wei et al., *Investigative Ophthalmol. And Visual Science*, 34:1814 (1993)). For example, only the corneal epithelial cells express keratin K12 (W. Y. W. Chen et al., *Current Eye Research* pp. 765-778 (1994)).

A major role of the conjunctiva is to provide ocular surface hydration and lubrication by producing tears from mucin producing goblet cells, as well as to provide a smooth and wet cellular surface to support the tear film on the corneal surface, which in turn results in an optically clear optical surface, and resultant clear vision. The conjunctiva thus supports the health of the corneal epithelium which is also essential for the maintenance of a clear, transparent cornea for clear vision. The corneal epithelium is totally dependent on a healthy conjunctival surface to maintain clear vision. Diseases or damage of the conjunctiva results in dryness and chronic inflammation of the entire ocular surface, leading to corneal epithelial destruction, gradual secondary damage and attrition of LSCs and eventual scarring and breakdown of the corneal epithelium, causing corneal stromal opacification, vascularisation, melting and resultant blindness. It is now clear, therefore that the integrity of LSC and the corneal epithelium requires a healthy conjunctiva.

These concepts of the ocular surface, the role of chronic inflammation and the role of limbal and conjunctival stem cells have only been recognized in recent years. The location of various stem cell populations is still undergoing investigation. (For example, there is still some question as to whether CSCs are present in the eyelid margins, as well as in the conjunctival fornix). See FIG. 1.

Ocular Surface Diseases are a group of disorders characterized by damage to either conjunctival or corneal epithelium, but the end result is a damaged, scarred corneal surface. Examples of ocular surface diseases include chemical and thermal burns to the eye, Stevens Johnson Syndrome (SJS) and ocular cicatricial pemphigoid (OCP). In all these disorders, in the acute event, both conjunctival and corneal epithelium are damaged, but often the initial damage occurs in the conjunctiva. Secondary damage to both LSCs and corneal epithelium then ensues as a later, chronic stage, and this causes blindness. The CSC is rarely damaged in these disorders, as these stem cells reside high up, or low down in the conjunctival fornices (where they are protected from chemical and thermal damage).

However, the current state of art focuses only on the corneal epithelium and LSCs. All the current literature on LSCs and limbal stem cell transplantation, including the previously cited papers by Tsai, Wei etc. all describe methods of growing and retransplanting LSCs, at a late stage in the disease process in which secondary corneal and LSC damage has occurred. In fact, some, like the Wei paper, initially tried to use conjunctival epithelium (not CSCs) to replace corneal epithelium, and stated it did not work, and they then suggested that limbal epithelium, containing LSCs was more successful in replacing corneal epithelium. The prior art in this area therefore stated that LSCs could be used to treat LSC deficiency which in turn restores a healthy corneal epithelium.

The present invention differs significantly in concept because we are using CSCs to repair conjunctival deficiency, not limbal deficiency. While the present method can be used to replace corneal epithelium (which can also be accomplished using LSCs), the present method also allows CSC transplantation to restore a healthy conjunctival surface. This in turn prevents secondary limbal and corneal damage and prevents secondary LSC deficiency. Many ocular surface diseases initiate with conjunctival damage, followed by secondary limbal and corneal damage. The present invention provides a surgical intervention at a much earlier stage in the disease process, to prevent limbal and LSC damage in the first place, before it happens, thus obviating the need for later LSC transplantation and corneal reconstruction. This earlier intervention is not available by use of LSC transplantation.

Another major difference between the present invention and the prior art represented by LSC transplantation is that CSCs and LSCs are located in completely different locations. LSCs are located in a narrow band around the cornea, while CSCs are either concentrated high up in the superior conjunctival fornix, or deep below in the inferior conjunctival fornix, in both cases far away from the limbal region of the eye, so the surgical technique also differs. Harvesting LSCs in the conventional manner described by Tsai and others will not take any CSCs, and to date, no one has described the technique of CSC harvesting. Any advertent inclusion of conjunctival epithelium adjacent to the site of LSC harvesting does not include the presence of CSCs. In addition, obtaining CSCs from the conjunctival fornix cannot result in subsequent corneal or limbal damage, unlike obtaining LSCs from the limbus which must result in some degree of focal limbal and corneal damage. Previous studies have shown that loss of the limbal stem cells even from an otherwise healthy cornea can be damaging.

In contrast to the prior art describing transplantation of limbal stem cells, the present invention specifically addresses conjunctival stem cell isolation, expansion and differentiation. The present invention is useful for providing cells and tissue equivalents for use in treating conjunctival diseases or trauma. The latter group of conditions are far more diverse and covers not only limbal deficiency-related ocular surface disorders (which limbal stem cell restoration will treat), but includes completely different indications (e.g. conjunctival reaconstruction after eye surgery such as pterygium excision, glaucoma, retinal and squint surgery), for which limbal transplantation is not indicated.

Furthermore, conjunctival stem cell transplantation for ocular surface disorders differs significantly from limbal stem cell transplantation. In many ocular surface disorders, the primary tissue that is damaged is the conjunctiva, and resulting complications from conjunctival injury, scarring and inflammation subsequently lead to limbal stem cell deficiency and secondary corneal damage.

The present invention treats ocular surface disorders at the much earlier stage of conjunctival deficiency, before secondary limbal deficiency ensures. For instance, Stevens Johnson syndrome (a disease characterized by conjunctival damage) has an initial acute stage in which severe loss of conjunctiva occurs from conjunctival blistering. At this stage, it is believed that minimal limbal stem cell damage occurs. After this acute stage, severe damage to the conjunctiva results in scarring, chronic inflammation, shrinkage and drying of the conjunctival surface (from conjunctival deficiency), eyelid distortion and exposure. These processes lead to persistent and chronic ocular surface inflammation, resulting in secondary limbal stem cell damage, corneal damage and loss of vision several months later, which may be prevented if conjunctival stem cell expansion and transplantation is performed prior to the occurrence of secondary limbal damage.

The present invention therefore cures the primary problem, i.e. that of conjunctival cell deficiency, which occurs in many forms of ocular surface disease. Simply curing the limbal stem cell deficiency may not work in the long-term, as the conjunctival factors damaging limbal stem cells are likely to remain if the conjunctival problem is not solved. Thus, the present invention prevents or reduces secondary limbal stem cell damage. Moreover, in the event that CSC transplantation to restore anatomical and functional integrity of the conjunctiva is not wholly successful and LSC transplantation is still required, the partial restoration of ocular surface integrity is likely to play a significant supportive role in survival of the LSC transplant itself.

The timing of conjunctival stem cell surgery significantly precedes limbal stem cell surgery and the indications for conjunctival stem cell surgery are wider than those for limbal stem cell surgery.

At certain parts of the culturing processs of the invention, cells are grown on a conventional substrate, human amniotic membrane. However, artificial substrates that can support epithelial tissue, in both the physical sense and also those that can promote tissue stratification and terminal differentiation, can be used at appropriate points in the process. For example, the cells can be grown on a permeable membrane as a physical support, which membrane can be transferred from one culture condition to another so that appropriate factors from the culture medium can be delivered to the cells to alternatively promote cell proliferation or differentiation of the proliferating cells to form tissue equivalents.

In one embodiment of the invention, nitrocellulose paper is formed into a frame surrounding an amniotic membrane. The conjunctival stem/epithelial cells are then grown upon the framed membrane support. In one embodiment of the invention, the cells are cultured on the surface of a basement membrane side of an amniotic membrane. Such amniotic membrane can be obtained, for example, from afterbirth tissues saved from patients undergoing elective Cesaerian section.

The culture media used in the present invention vary according to the stage of the cells in the process from biopsy of the tissue through outgrowth of the cells (primary culture) and expansion of their numbers (proliferative culture) and differentiation of the cells and formation of a tissue equivalent (differentiative culture). The medium for primary culture has the function of maintaining the viability and proliferation and differentiation capacity of the conjunctival stem cells during dissolution of the tissue sample and migration of the stem cells out of the tissue sample. The inclusion of serum in an amount of from 5 to 10% of the volume of the culture medium and the use of a calcium ion ($Ca^{2+}$) concentration of from 0.7 to 1.1 mM, preferably about 0.9 mM, are important for these functions.

The medium for the proliferative culture maintains the viability and differentiation capacity of the conjunctival stem cells and also provides the factors the cells require to grow and divide and so increase in number. The proliferative medium also performs a function of allowing preferential growth of epithelial cells over fibroblast cells. The use of pituitary extract (preferably bovine pituitary extract) and omission of serum, and decrease of the calcium ion concentration to 0.03 to 0.3 mM (preferably from 0.12 to 0.17 mM, typically 0.15 mM) are important to the functions of the proliferative culture medium.

The differentiative culture medium supports the viability of the cells and also provides the factors that promote differentiation of the cells to express an epithelial cell phenotype. An increase in calcium ion concentration, preferably to 1.1 to 1.4 mM (preferably about 1.3 mM) in comparison to the amount in the proliferative medium, is important to the functions of the differentiation medium.

Epidermal Growth Factor (EGF), insulin and hydrocortisone are present in all three media used in the present invention. These ingredients promote the selection of conjunctival epithelial cells over fibroblasts during the culturing process.

The process of the present invention is preferably applied to the creation of conjunctival tissue equivalents. However, the present invention can also be applied to growth and differentiation of epitheloid cells generally. The invention can be applied to all ocular surface epithelial cells, such as limbal cells and corneal epithelial cells. The present invention can also be applied to the growth and differentiation of goblet cells and to keratinocytes.

A distinction between the present invention and the prior art is the selection of conjunctival tissue biopsy as the source of cells to be used in the invention. The selection of conjunctival stem cells as the starting cell type results in production of a tissue equivalent that is transparent and lacks a cornified striatum on its surface, such as occurs when keratinocytes are used to create skin tissue equivalents. This should be contrasted with the results of the prior art as described by Pelligrini et al., supra, who indicates that restoration of the corneal surface by conjunctiva transplanted directly onto the corneal surface, is totally inadequate, leading to "neovascularisation, chronic inflammation, recurrent epithelial defects and stromal scarring" of the cornea. These problems are avoided by the present invention, which provides conjunctival equivalents that, upon transplantation on the conjunctival surface of the eye, restore the functional integrity of the conjunctiva, thus protecting the corneal epithelial surface, and therefore do not lead to "neovascularisation, chronic inflammation, recurrent epithelial defects and stromal scarring".

The cells that result from the application of the present invention to conjunctival stem cells as the starting cells express characteristics of the epithelial cell phenotype. In particular, the cells are cobblestone shaped when attached to a surface. This shape is in contrast to the stellate or spindle shape exhibited by fibroblast cells. Furthermore, the conjunctival epithelial cells obtained by the invention express cytokeratin K4, a marker for non-keratinized, stratified epithelia, as is the case for the conjunctival epithelia (K. L. Krenzer and T. F. Freddo. *Investigative Ophthalmology and Visual Science* 38:142 (1997)). The conjunctival epithelial cells obtained are also negative for expression of the corneal specific cytokeratin, K3 (A. Schermer et al (*The Journal of Cell Biology* 103:49 (1986)).

The cells obtained by the present invention also form a stratified squamous epithelium after transplantation into the eye of a subject. This layered tissue structure is shown in FIGS. 5A, 5B, 5C, 4B, 6A and 6B.

Culture media used in the present invention comprise a basal medium and various supplements. A preferred medium for the primary culturing step comprises:

a) Dulbecco's Modified Essential Medium and Ham's F-12 medium in a ratio of 1:1;
b) Fetal Bovine Serum or Human Serum Albumin;
c) human Epidermal Growth Factor
d) insulin;
e) cholera toxin;
f) hydrocortisone;
g) an antibiotic or mixture of antibiotics;

In the primary culture medium, the amounts of these ingredients are preferably in the range of b) 5 to 15% Serum (preferably Fetal Bovine Serum or Human Serum Albumin);
c) 5 to 15 ng/ml Epidermal Growth Factor (preferably human)
d) 2 to 10 µg/ml insulin (preferably human);
e) 7 to 10 ng/ml cholera toxin;
f) 0.3 to 1 µg/ml hydrocortisone;
g) 10 to 100 µg/ml of an antibiotic or mixture of antibiotics.

In the primary culture medium, calcium ion ($Ca^{2+}$) is typically included at a concentration of from 0.7 to 1.1 mM, preferably about 0.9 mM.

A preferred medium for the proliferative culturing comprises:

a) Keratinocyte Growth Medium;
b) Epidermal Growth Factor (preferably human);
c) insulin (preferably human);
d) hydrocortisone;
e) pituitary extract (typically bovine);
f) an antibiotic or mixture of antibiotics;

In a preferred medium for the proliferative culturing the amounts of these ingredients are:

b) 5 to 15 ng/ml human Epidermal Growth Factor;
c) 2 to 10 µg/ml insulin;
d) 0.3 to 1 µg/ml hydrocortisone;
e) 15 to 140 µg/ml, preferably 15 to 120 µg/ml, more preferably from 15 to 100 µg/ml, still more preferably from 15 to 70 µg/ml of pituitary extract; ranges from 30 to 100 µg/ml or from 50 to 100 µg/ml or 70 to 100 µg/ml area also acceptable;
f) 10 to 100 µg/ml of an antibiotic or mixture of antibiotics.

In the proliferative culturing medium, calcium ion is typically present at a concentration to 0.03 to 0.3 mM, preferably from 0.12 to 0.17 mM, more preferably 0.15 mM. Also, using higher amount of pituitary extract typically allows better colony forming efficiency and more rapid proliferation.

A preferred medium for the differentiative culturing comprises:

a) Dulbecco's Modified Essential Medium and Ham's F-12 medium in a ratio of 3:1;
b) Fetal Bovine Serum or Human Serum Albumin;
c) Epidermal Growth Factor (preferably human)
d) insulin (preferably human);
e) cholera toxin;
f) hydrocortisone;
g) an antibiotic or mixture of antibiotics.

In a preferred medium for the differentiative culturing the amounts of these ingredients are:

b) 0.5 to 5.0% Fetal Bovine Serum or Human Serum Albumin;
c) 5 to 15 ng/ml human Epidermal Growth Factor
d) 2 to 10 µg/ml insulin;
e) 7 to 10 ng/ml cholera toxin;
f) 0.3 to 1 µg/ml hydrocortisone;
g) 10 to 100 µg/ml of an antibiotic or mixture of antibiotics.

In the medium used for differentiative culturing, calcium ion is typically included at a concentration of from 1.1 to 1.4 mM, preferably about 1.3 mM.

In the above media, Keratinocyte Growth Medium is MCDB 153 medium or a modification thereof available from Clonetics as "Keratinocyte Growth Medium". MCDB 153 medium has the following components:

| Component | g/L |
|---|---|
| Ammonium Metavanadate | 0.000000585 |
| Calcium Chloride-$2H_2O$ | 0.004411 |
| Cupric Sulfate-$5H_2O$ | 0.00000275 |
| Ferrous Sulfate-$7H_2O$ | 0.00139 |
| Magnesium Chloride | 0.05713 |
| Manganese Sulfate | 0.000000151 |
| Molybdic Acid-$4H_2O$ (ammonium) | 0.00000124 |
| Nickel Chloride-$6H_2O$ | 0.00000012 |
| Potassium Chloride | 0.11183 |
| Sodium Acetate (anhydrous) | 0.30153 |
| Sodium Chloride | 7.599 |
| Sodium Metasilicate-$9H_2O$ | 0.000142 |
| Sodium Phosphate Dibasic (anhydrous) | 0.284088 |
| Sodium Selenite | 0.0000038 |
| Stannous Chloride-$2H_2O$ | 0.000000113 |
| Zinc Sulfate-$7H_2O$ | 0.000144 |
| L-Alanine | 0.00891 |
| L-Arginine-HCl | 0.2107 |
| L-Asparagine-$H_2O$ | 0.015 |
| L-Aspartic Acid | 0.00399 |
| L-Cysteine-HCl—$H_2O$ | 0.04204 |
| L-Glutamic Acid | 0.01471 |
| L-Glutamine | 0.8772 |
| Glycine | 0.00751 |
| L-Histidine-HCl—$H_2O$ | 0.01677 |
| L-Isoleucine | 0.001968 |
| L-Leucine | 0.0656 |
| L-Lysine-HCl | 0.01827 |
| L-Methionine | 0.00448 |
| L-Phenylalanine | 0.00496 |
| L-Proline | 0.03453 |
| L-Serine | 0.06306 |
| L-Threonine | 0.01191 |
| L-Tryptophan | 0.00306 |
| L-Tyrosine-2Na | 0.00341 |
| L-Valine | 0.03513 |
| D-Biotin | 0.0000146 |
| Choline Chloride | 0.01396 |
| Folic Acid | 0.00079 |
| myo-Inositol | 0.01802 |
| Niacinamide | 0.00003663 |
| D-Pantothenic Acid (hemicalcium) | 0.000238 |
| Pyridoxine-HCl | 0.00006171 |
| Riboflavin | 0.0000376 |
| Thiamine-HCl | 0.000337 |
| Vitamin B-12 | 0.000407 |
| Adenine-HCl | 0.03088 |
| D-Glucose | 1.081 |
| HEPES | 6.6 |
| Phenol Red-Na | 0.001242 |
| Putrescine-2HCl | 0.000161 |
| Pyruvic Acid-Na | 0.055 |
| Thioctic Acid | 0.000206 |
| Thymidine | 0.000727 |

For the antibiotics used in the various media, in medium I, the antibiotic or mixture of antibiotics preferably comprises 40 to 60 IU/ml of penicillin and 40 to 60 μg/ml of streptomycin. In medium II, the antibiotic or mixture of antibiotics preferably comprises 40 to 60 μg/ml of Gentamicin and 40 to 60 ng/ml of Amphotericin B; and in medium III the antibiotic or mixture of antibiotics preferably comprises 40 to 60 IU/ml of penicillin and 40 to 60 μg/ml of streptomycin.

The present invention also encompasses conjunctival equivalents produced by the process of the invention. The conjunctival tissue equivalent obtained by the present invention preferably forms a stratified squamous epithelium comprising several layers of conjunctival epithelial cells. Preferably the layers are connected by one or more desmosome structures formed between adjacent cells in each layer.

The present invention further encompasses methods for treatment of eye disorders by autologous or heterologous transplantation of such conjunctival equivalents into the eye of a subject. For use in transplantation the conjunctival tissue equivalents obtained by the culturing process of the invention are typically transplanted to the ocular surface, usually the sclera, forniceal or tarsal areas, as a tissue engineered substitute for normal bulbar, forniceal or tarsal conjunctiva. The conjunctival equivalents can be placed in existing conjunctiva on the inner surface of the eyelid.

These embodiments stand in contrast to methods of the prior art that relate to transplantation of limbal tissue equivalents formed by culture of limbal stem cells. In the prior art, the limbal tissue equivalents are only transplanted directly onto the cornea.

However, the conjunctival tissue equivalents of the invention can also be used to replace, support or reinforce epithelium of the ocular surface at any location on the ocular surface including areas that are adjacent to the cornea. These embodiments of the invention can also be achieved using tissue equivalents grown according to the inventions using explants of tissue obtained from other parts of the ocular surfaces.

The multi-step culture procedure of the invention produces the desirable result of producing a large population of conjunctival epithelial cells, typically in the form of an organized tissue equivalent. The organized tissue equivalent in typically comprises conjunctival epithelial cells in a multilayered arrangement and in one preferred embodiment will include goblet cells interspersed among the epithelial cells. Goblet cells are characterized by being ellipsoid in shape and containing large secretory granules containing mucin. Goblet cells also stain with PAS stain.

The present invention offers several advantages compared to conventional methods for culturing epithelial cells. The conventional method of tissue culture gives rise to epithelial cells of a normal phenotype, however, it has the disadvantage that it requires the use of serum and 3T3 feeder cells (which are fibroblasts with an extended life-span obtained from Swiss mice). The use of serum (of bovine origin) has disadvantages associated with the risk of infection (e.g. Creutzfeldt-Jacob disease or Mad Cow disease). In the present invention bovine serum can be replaced with human serum albumin or omitted entirely, greatly reducing the risk of contamination of the conjunctival equivalents with pathogens.

The use of the conventional serum-containing media is often combined with the use of 3T3 feeder cells. This allows the keratinocyte (skin cells) compartment to continue to proliferate. By avoiding the use of 3T3 cells, our clients are eliminating the requirement for animal products and tissue, which may introduce infection, e.g. by retroviruses, as well as potentially contribute towards graft failure due to the use of these xenografts (grafts obtained from species other than humans).

The present method omits use of any feeder cell layer and so these disadvantages are avoided.

The use of conventional serum-containing media without the feeder cells also results in significant overgrowth of fibroblast cells, preventing the obtaining of pure populations of conjunctival epithelial cells. Conversely, by use of serum-free culture conditions with its low calcium concentration, the present invention favors the growth of conjunctival epithelial cells over fibroblasts, thus allowing a more consistent cultures having negligible contamination with fibroblasts.

The differentiation culturing step (stratification and differentiation) is important to promote the differentiation of the epithelial cells, as well as enhancing the formation of cell-to-cell interaction. The presence of desmosomes, apical microvilli, and a normal cytoskeleton in the conjunctival tissue equivalents is seen by electron microscopic examination. Inclusion of a differentiation culturing step enhances the stability of the tissue construct, which was important for clinical transplantation. In the absence of the differentiative culturing step, cells are more undifferentiated, less stratified, less adherent, and the tissue equivalent as a whole is less stable. The epithelial cells are more likely to break apart during the transplantation process and during the subsequent recovery period of the patient. On the other hand, inclusion of the differentiative culturing step provides a more stable tissue equivalent that results in a more successful clinical outcome.

The present invention also provides an indication of CSC transplantation, completely different from indications for LSC transplantation. CSC transplantation has additional uses in ophthalmic surgery, namely to replace diseased or surgically-damaged conjunctival surfaces not directly related to conventional Ocular Surface Disorders. Examples of these would be:

1. Pterygium Surgery. Pterygium surgery is described in detail in *The University of Miami Bascom Palmer Eye Institute Atlas of Ophthalmology*, R. K. Parrish, Jr., ed., c. 2000 by Butterworth Heinemann, Philadelphia, Pa., in Chapter 22 at p. 161 and FIGS. 22-24. In this form of surgery, removal of a pterygium mass from the conjunctiva leaves a large conjunctival defect, which is currently replaced by a large autologous graft from under the eyelid, which then leaves yet another conjunctival defect elsewhere. Growing conjunctiva prior to pterygium surgery allows a surgeon to utilize this extra sheet of conjunctiva without resorting to damaging another large area of conjunctiva under the eyelid.

2. Glaucoma surgery—there are 2 major forms of glaucoma surgery, both of which require healthy conjunctiva integral to success:
   a. Trabeculectomy—a drainage valve is surgically made in the sclera, adjacent to the limbus, where aqueous fluid is allowed to escape under the conjunctiva, which balloons out forming a conjunctival bleb. This procedure however has a significant failure rate, requiring repeat surgery in this area to reopen the valve, and in so doing, overlying conjunctiva is further scarred or damaged, contributing to surgical failure. Also, sometimes conjunctival blebs develop a hole, causing leakage of aqueous fluid out of the surgical site with a subsequent risk of infection. In both instances, revision surgery is necessary, and is limited in success by an inadequate supply of healthy conjunctiva. Growing autologous conjunctiva prior to revision surgery will allow surgeons to perform revision surgery with adequate conjunctiva and therefore enhance surgical success. The biopsy site to obtain CSCs lies in the upper or lower fornix and is sufficiently distant from the trabeculectomy site, which is usually sited at the superior bulbar conjunctiva, is closely related to the superior limbal margin.

b. Seton surgery—in advanced or high risk cases of glaucoma (usually after failed repeated trabeculectomies), a drainage implant is placed beneath the conjunctiva adjacent to the limbus. These implants, which are shaped in the form of a flat plate with a tube leading out from the anterior chamber, rely on normal conjunctiva to cover the implant and hold it in place. In many cases of advanced glaucoma, previous surgery will have scarred large areas of conjunctiva, and it may not be possible to dissect free enough conjunctiva to lodge these implants safely to prevent extrusion. Again, growing conjunctiva to augment conjunctival coverage will be useful and enhance this form of surgery.

3. Squint surgery and retinal detachment surgery—in both these forms of surgery, procedures are performed on either the extraocular muscles (squint surgery) or on the surface of the sclera (retinal surgery). To gain access, conjunctiva must be reflected away to reach these structures, and replaced after the surgery is complete. In cases of previous similar surgery, overlying conjunctiva is scarred and stuck down to sclera and reattempts to reflect conjunctiva for repeat surgery often results in loss of useful, healthy conjunctiva which cannot be adequately replaced after the procedure. Here again, preparation of conjunctival tissue equivalents for replacement of the damaged area prior to re-operations would provide a better outcome of the surgery.

The present invention may also find application in other less frequent, but often critical medical situations, such as ocular trauma repair, tumor excisions and orbital surgery in which conjunctiva is severely damaged, and the availability fo conjunctival equivalents would reduce surgical difficulty and the incidence of postoperative complications in these procedures.

EXAMPLES

The present invention is illustrated by the following examples, which are intended to illustrate, not to limit, the scope of the invention. The scope of the invention is rather defined by the claims following.

Example 1

Conjunctival Stem Cell Biopsy

Conjunctival stem cell biopsies are performed for patients who are selected to undergo the autologous transplantation of cultivated conjunctival cells procedure. Conjunctival stem cell biopsy is performed 2 weeks prior to the transplantation operation. The procedure is carried out under aseptic conditions. The eyelids are cleaned with 50% Povidone Iodine solution. Topical amethocaine eye drops are applied to the ocular surface as a local anesthetic. A standard lid speculum is placed. Under an operating microscope, a superior limbal corneal stay suture (7/0 Vicryl) is placed, followed by inferior globe retraction to expose the superior conjunctival fornix. Local infiltration of the fornix is carried out with subconjunctival lignocaine 2% using a 270 needle. A biopsy of forniceal conjunctival epithelium measuring 1 mm×3 mm is performed. A second similarly sized biopsy may be obtained adjacent to the original biopsy site to allow for duplication of stem cell culture in the event of lack of growth or contamination of one specimen. The biopsy site should be as high as possible, at the forniceal junction, in order to attain a maximal density of conjunctival stem cells. The epithelium is dissected free from the underlying stroma, and the tissue is placed in DMEM and immediately sent to the laboratory for culture. Hemostasis is secured with bipolar diathermy. A subconjunctival dexamethasone/gentacicin injection is given. The patient is discharged with Tobradex eyedrops q.d.s. for 1 week.

Example 2

Cultivation Of Conjunctival Epithelial Cells and Use Thereof for Producing Human Conjunctival Equivalents In Vitro Human Amniotic Membrane Preparation Human amniotic membranes were cut into 2-3 square centimeter pieces and placed on nitrocellulose filter papers (Millipore, Inc.) with the basement-membrane side up. They were preserved in 50% Dulbecco's Modified Eagle's Medium (DMEM) and 50% glycerol and stored at −80° C.

Thawing of Amniotic Membrane

A bottle containing a sheet of frozen human amniotic membrane was removed from storage. The membrane was thawed quickly by placing the bottle in a 37° C. water bath. Using non-toothed forceps, the membrane was removed from the container and placed in a 60 mm dish containing Phosphate Buffered Saline (PBS). The membrane was rinsed twice with PBS solution containing 100 IU/ml penicillin, 100 μg/ml streptomycin and 5 μg/ml Amphotericin B for 10 minutes. The membrane was then incubated with Dispase 1.2 U/ml for 30 minutes at 37° C., 95% air, 5% $CO_2$ to remove any amniotic epithelial cells which might interfere with the subsequent growth of the conjunctival epithelial cells.

The dish was removed from the incubator and the basement membrane surface was rubbed gently with small sponges to dislodge any remnant amniotic epithelial cells. Care was taken to ensure that the amniotic membrane was minimally traumatized and handled, so as to prevent damage or tearing of the membrane. The dispase was rinsed off with 3 washes of PBS and 1 wash of DMEM. The amniotic membrane was then transferred to another square piece of nitrocellulose paper with a central window cut out. The size of the nitrocellulose membrane depends on the area of transplantation required (usually 2.5 cm×2.5 cm in size). The central window is to permit easy visualization and monitoring of the growth of epithelial cells on the membrane surface. Care was taken to ensure that the amniotic membrane is placed basement-membrane side up. The membrane was then immersed in DMEM and kept in the incubator for 24 hours at 37° C., 95% air, 5% $CO_2$.

Isolation and Cultivation of Human Conjunctival Epithelial Cells

Culture Media and Reagents

The following culture media and reagents were used in the culture process:

Dulbecco's modified Eagles's medium (DMEM), Hank's balanced salt solution, human epidermal growth factor (hEGF), penicillin, streptomycin, amphotericin B, trypsin, ethylenediaminetetraacetic acid (EDTA) were obtained from Gibco. Insulin, hydrocortisone, bovine pituitary extract, cholera toxin were obtained from Sigma. Keratinocyte Growth Medium, gentamicin, and amphotericin B were obtained from Bio Whittaker/Clonetics. Fetal bovine serum (FBS) was obtained from Hyclone.

The following culture media were used.

Culture Medium 1
 a. DMEM and Hams F-12 in a 1:1 ratio
 b. 10% Fetal bovine serum
 c. 10 ng/ml human Epidermal Growth Factor
 d. 5 µg/ml Insulin
 e. 8.4 ng/ml Cholera toxin
 f. 0.4 µg/ml Hydrocortisone
 g. 50 IU/ml Penicillin
 h. 50 µg/ml Streptomycin Culture Medium 2 (Serum-Free Medium)
 a. Keratinocyte Growth Medium (a modified MCDB 153 culture media)
 b. 10 ng/ml human Epidermal Growth Factor
 c. 5 µg/ml insulin
 d. 0.5 µg/ml hydrocortisone
 e. 30 µg/ml bovine pituitary extract
 f. 50 µg/ml Gentamicin
 g. 50 ng/ml Amphotericin B Culture Medium 3
 a. DMEM and Hams F-12 in a 3:1 ratio
 b. 2.5% Fetal bovine serum
 c. 10 ng/ml human Epidermal Growth Factor
 d. 5 µg/ml Insulin
 e. 8.4 ng/ml Cholera toxin
 f. 0.4 µg/ml Hydrocortisone
 g. 50 IU/ml Penicillin
 h. 50 µg/ml Streptomycin HAM Preparation Prior to Use Prior to use of the membrane, the epithelial cell culture medium 1 was warmed to 37° C. The membrane, with the nitrocellulose paper support, was rinsed twice with the pre-warmed culture medium 1 and subsequently transferred to a 35 mm dish immersed in the culture media.

Cultivation of Conjunctival Epithelial Cells on Amniotic Membrane

The conjunctival tissue is immediately processed. The conjunctival tissue was removed from the transportation container and placed on a 60 mm dish containing PBS. Using fine dissection forceps and a scalpel, the conjunctival tissue was cut into 0.5 mm size pieces. These pieces (explants) are place on the basement-membrane side of the amniotic membrane. Culture media 1 was carefully added with a micropipette tip slowly so that each explant was partially submerged. The cells are incubated at 37° C., under 5% $CO_2$ and 95% air. This medium was used for 24 to 48 hours during which migration of epithelial cells from the explant onto the membrane was achieved. The medium was then changed to culture medium 2 and the explants fully submerged in this media. The medium was changed every 2 days, care being taken not to dislodge the explants.

Within 10 to 12 days, the epithelial cells grew to form a confluent sheet of cells over the amniotic membrane. When confluence was achieved, the medium was changed to culture medium 3 for 2 to 4 days to promote further proliferation, stratification and differentiation. The conjunctival equivalent thus established was then ready for transplantation.

Results

Cells cultivated in serum-free media had a colony-forming efficiency of 14.5% and 10.9% for $2^{nd}$ and $3^{rd}$ passages respectively. The use of feeder layers with serum-free media did not improve the proliferative capacity of the cells (mean colony-forming efficiency for $2^{nd}$ and $3^{rd}$ passages, 10.1% and 6.0% respectively). Serum-containing media with 3T3 feeder layers had a colony-forming efficiency of 20.6% and 14.2% for $2^{nd}$ and $3^{rd}$ passages, respectively.

With serum-free media, epithelial cells could be cultivated an average of 6 passages and underwent 26.9±8.0 cell divisions before undergoing senescence. Co-culturing with feeder layers did not enhance the proliferative capacity of these cells and they could only be cultivated an average of 4 passages and undergo 19.2±7.9 cell divisions. Serum-containing media with feeder layers allowed cells to be cultivated an average of 8 passages, and undergo 36.5±9.9 cell divisions.

Ex-vivo expansion of conjunctival epithelial cells resulted in confluent epithelial sheets on the human amniotic membranes. Light microscopic examination revealed 2 to 6 layers of stratified squamous conjunctival epithelial cells with progressive flattening of the cells from the basal layer upwards. Ultrastructural examination revealed apical microvillus extensions and numerous desmosomes. The cultivated cells demonstrated a normal conjunctival cytokeratin expression (K4 positive and K3 negative, FIG. 5B, 5C).

Example 3

Transplantation of Autologous Cultured Conjuntival Equivalents for Pterygium Surgery and Ocular Surface Reconstruction Methods Transplantation of autologous conjunctival equivalents was carried out in 25 eyes of 24 patients requiring ocular surface surgery: 23 patients had pterygium, 1 patient had an extensive conjunctival nevus, and 1 patient had a persistent leaking glaucoma bleb fistula requiring conjunctival bleb reconstruction. Conjunctival forniceal stem cell biopsies (measuring 1×3 mm) were obtained 2 weeks prior to definitive surgery and transplantation of the tissue-equivalent, using the method of Examples 1 and 2. The amount of bovine pituitary extract typically used in the culture medium 2 was 30 µg/ml. In some instances 100 to 140 µg/ml of bovine pituitary extract was used. The results are comparable using either concentration, but the lower concentration has the advantage of using less bovine (non-human origin) material.

The conjunctival explants obtained were cultivated on human amniotic membranes in serum-free conditions for a mean of 15 days by the method of Example 2. At the time of definitive surgery, the pterygia and diseased conjunctiva were excised, and the autologous cultured conjunctival tissue-equivalents were transplanted over the conjunctival defects Pterygium Excision and Transplantation of Conjunctival Equivalent These procedures were performed under topical anesthesia and in the operating theatre with the use of an operating microscope. The eyelids were cleaned with 50% Providone Iodine solution. Anethesia consists of either topical amethocaine eyedrops applied to the ocular surface, peribulbar or retrobulbar anesthesia. A standard lid speculum was placed. A superior limbal corneal stay suture (7/0 Vicryl) was placed, and excision of the pterygium according to the bare sclera technique was performed and hemostasis secured.

The conjunctival equivalent, including the amniotic membrane/nitrocellulose membrane support, was rinsed 2 times with balanced salt solution. Using non-toothed forceps, this composite sheet was transferred to the patient's eye over the bare scleral defect using the nitrocellulose sheet as a support. The conjunctival equivalent was sutured in place with interrupted 10/0 Vicryl sutures. An additional amniotic membrane patch graft, exceeding the conjunctival equivalent size by 2 mm, was placed over the conjunctival equivalent, basement membrane facing downwards, to act as a protective patch. Subconjunctival dexamethasone/gentamicin was administered. Post-operatively, the patient was given preservative-free antibiotic-steroid eyedrops q.d.s. for 1 week with a tailing-down dose over the following 3 weeks. The amniotic membrane patch was removed at about 3-5 days after surgery, to reveal a healthy and stable conjunctival equivalent transplant at the site of the previously excised pterygium. Complete epithelialization was confirmed by the absence of fluorescein staining within 1 to 5 days following surgery.

The invention being thus described, certain modifications of the materials and methods used to embody the invention will be apparent to one of ordinary skill in the art. Such modifications are to be considered within the scope of the invention as claimed below.

The present application includes citations to the patent and periodical publication literature. These papers are hereby incorporated by reference in their entirety for all purposes by such citation.

What is claimed is:

1. A method for producing conjunctival tissue equivalents comprising:
   i) culturing cells of a tissue comprising conjunctival stem cells in a medium I comprising
      a) Dulbecco's Modified Essential Medium and Ham's F-12 medium in a ratio of 1:1;
      b) Fetal Bovine Serum or Human Serum Albumin;
      c) human Epidermal Growth Factor
      d) insulin;
      e) cholera toxin;
      f) hydrocortisone;
      g) an antibiotic or mixture of antibiotics;
   ii) further culturing the cells in a medium II comprising:
      a) Keratinocyte Growth Medium;
      b) human Epidermal Growth Factor;
      c) insulin;
      d) hydrocortisone;
      e) pituitary extract;
      f) an antibiotic or mixture of antibiotics; and
   iii) further culturing the cells to obtain conjunctival tissue equivalents in a medium III comprising:
      a) Dulbecco's Modified Essential Medium and Ham's F-12 medium in a ratio of 3:1;
      b) Fetal Bovine Serum or Human Serum Albumin;
      c) human Epidermal Growth Factor
      d) insulin;
      e) cholera toxin;
      f) hydrocortisone;
      g) an antibiotic or mixture of antibiotics;
   said culturing steps (i), (ii), (iii) being performed on the surface of a basement membrane side of an amniotic membrane; thereby obtaining a conjunctival tissue equivalent.

2. A method for producing equivalents of an ocular tissue comprising:
   i) culturing explants of tissue from the ocular surface in a medium I comprising
      a) Dulbecco's Modified Essential Medium and Ham's F-12 medium in a ratio of 1:1;
      b) Fetal Bovine Serum or Human Serum Albumin;
      c) human Epidermal Growth Factor
      d) insulin;
      e) cholera toxin;
      f) hydrocortisone;
      g) an antibiotic or mixture of antibiotics;
   ii) culturing cells from the explant in a medium II comprising:
      a) Keratinocyte Growth Medium;
      b) human Epidermal Growth Factor;
      c) insulin;
      d) hydrocortisone;
      e) pituitary extract;
      f) an antibiotic or mixture of antibiotics;
   iii) culturing the cells to obtain conjunctival tissue equivalents in a medium III comprising:
      a) Dulbecco's Modified Essential Medium and Ham's F-12 medium in a ratio of 3:1;
      b) Fetal Bovine Serum or Human Serum Albumin;
      c) human Epidermal Growth Factor
      d) insulin;
      e) cholera toxin;
      f) hydrocortisone;
      g) an antibiotic or mixture of antibiotics;
   thereby obtaining an equivalent of said ocular tissue.

3. The method of claim 2, wherein said tissue comprises corneal epithelial cells or limbal stem cells.

4. The method of claim 2, in which the tissue from an ocular surface comprising conjunctival stem cells is obtained by biopsy of tissue distal from the cornea in a manner that the cornea remains intact.

5. A method for producing equivalents of an ocular tissue comprising:
   culturing explants of tissue comprising conjunctival stem cells in a medium I comprising
      a) Dulbecco's Modified Essential Medium and Ham's F-12 medium in a ratio of 1:1;
      b) Fetal Bovine Serum or Human Serum Albumin;
      c) human Epidermal Growth Factor
      d) insulin;
      e) cholera toxin;
      f) hydrocortisone;
      g) an antibiotic or mixture of antibiotics;
   ii) culturing cells from the explant in a medium II comprising:
      a) Keratinocyte Growth Medium;
      b) human Epidermal Growth Factor;
      c) insulin;
      d) hydrocortisone;
      e) pituitary extract;
      f) an antibiotic or mixture of antibiotics; and
   iii) culturing the cells to obtain ocular tissue equivalents in a medium III comprising:
      a) Dulbecco's Modified Essential Medium and Ham's F-12 medium in a ratio of 3:1;
      b) Fetal Bovine Serum or Human Serum Albumin;
      c) human Epidermal Growth Factor
      d) insulin;

e) cholera toxin;
f) hydrocortisone;
g) an antibiotic or mixture of antibiotics;
thereby obtaining an equivalent of said ocular tissue.

6. The method of claim 5, in which the tissue comprising conjunctival stem cells is obtained by biopsy of tissue distal from the cornea in a manner that the cornea remains intact.

* * * * *

UNITED STATES PATENT AND TRADEMARK OFFICE
CERTIFICATE OF CORRECTION

PATENT NO. : 7,611,895 B2
APPLICATION NO. : 11/398557
DATED : November 3, 2009
INVENTOR(S) : Tan et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 519 days.

Signed and Sealed this

Twelfth Day of October, 2010

David J. Kappos
*Director of the United States Patent and Trademark Office*